United States Patent [19]
Janis et al.

[11] Patent Number: 5,328,830
[45] Date of Patent: Jul. 12, 1994

[54] POTASSIUM CHANNEL MODULATORS

[75] Inventors: Ronald A. Janis, Orange; Frederick J. Hoffman, Jr., Madison, both of Conn.

[73] Assignee: Miles Inc., West Haven, Conn.

[21] Appl. No.: 941,004

[22] Filed: Sep. 8, 1992

[51] Int. Cl.$^5$ .......................................... G01N 33/567
[52] U.S. Cl. ..................................... 435/7.21; 435/7.8; 435/948; 435/968
[58] Field of Search ........................ 435/7.21, 7.8, 948, 435/968

[56] References Cited

U.S. PATENT DOCUMENTS 4,567,188  1/1986  Niemers et al. ...................... 514/342

OTHER PUBLICATIONS

Bray et al., 1992, J. Biol. Chem., 267:11689 "A Specific Binding Site for K+ Channel Openers in Rat Aorta".
Quast et al., 1992, Japanese J. Pharm., 58:226P, "Identification of a Specific Binding Site for K+".
"Channel Openers in Rat Aorta".
French et al., Modulation of [$^3$H] Glibenclamide Binding to Cardiac and Insulinoma Membranes. Eur. J. Pharmacology 207(1):23–28, 1991.

Primary Examiner—Esther L. Kepplinger
Assistant Examiner—Donna C. Wortman

[57] ABSTRACT

An assay for detecting molecules and compounds which specifically bind to sites which regulate cellular potassium channels, for use, inter alia, as a method for identifying drugs with activity specific for modulating K+ channels.

5 Claims, 4 Drawing Sheets

POTASSIUM CHANNEL MODULATORS

FIELD OF THE INVENTION

The present invention relates to methods for detecting specific activity of compounds. More particularly, the present specification discloses assays for detecting the binding of molecules and compounds to sites that regulate potassium channels.

BACKGROUND

The concentration of intracellular free calcium ($Ca^{2+}$) is a major determinant of smooth muscle contraction. The influx of $Ca^{2+}$ through voltage-sensitive $Ca^{2+}$ channels into cells is an important mechanism for increasing intracellular $Ca^{2+}$ concentration. Voltage-sensitive L-type $Ca^{2+}$ channels are opened when cells depolarize. In sum, depolarization of a smooth muscle cell correlates with its contraction via influx of calcium ions.

The tendency for potassium ($K^+$) to exit out of a cell is responsible for the cell's resting membrane potential. The opening of $K^+$ channels increases the net negative charge of a resting cell (or hyperpolarizes it), and thereby, tends to make it more difficult to depolarize. In fact, when $K^+$ channels are opened, depolarized cells will repolarize. Thus, the opening of $K^+$ channels counteracts cellular depolarization, and therefore, prevents or reverses smooth muscle contraction.

"$K^+$ channel openers" are a chemically heterogeneous group of compounds that hyperpolarize cells and thereby decrease excitability and inhibit the influx of $Ca^{2+}$ into cells. $K^+$ channel openers have proven efficacy as antihypertensive agents (Edwards et al., 1990, Pharmac. Ther., 48:237), and are potentially useful in the treatment of diseases whose etiology is due to excessive membrane excitability or excessive intracellular calcium levels.

An intact tissue assay for binding activity of $K^+$ channel openers has been reported. Bray et al., 1992, J. Biol. Chem., 267:11689, report the binding of a putative $K^+$ channel opener in rings cut from rat aorta. Intact tissue assays involve the use of large numbers of live animals which have to be maintained and sacrificed each time such assays are performed. Such assays are, therefore, cumbersome.

Furthermore, intact tissue assays have large variability in results because of inherent problems in washing nonspecifically associated radioligand out of the test tissue. For example, the assay disclosed in Bray et al. exhibited high variability which necessitated the carrying out of measurements in quadruplicate.

Thus, there is a need in the art for more efficient assays for detecting compounds which modulate $K^+$ channels. The present specification discloses for the first time, the specific binding of a $K^+$ channel opener, (+)-N-(2-ethoxyphenyl)-N'-(1,2,2,-trimethylpropyl)-2-nitroethene-1,1-diamine (hereinafter "CMPD-I"), to intact cells. The synthesis of the racemate (+/−) of this compound is disclosed in U.S. Pat. No. 4,567,188 issued to Niemers et al. (see FIG. 1). The preferred radioligand used in the present assays is the tritiated (+)enantiomer (hereinafter "[$^3$H]CMPD-I").

SUMMARY OF THE INVENTION

The present invention is directed, inter alia, to a binding assay that can be used to detect compounds (both agonists and antagonists) that bind to a site that regulates cellular function through $K^+$ channels. In particular, the present assays detect compounds that bind to a site that regulates the relaxation of smooth muscle induced by an action on $K^+$ channels sensitive to CMPD-I.

Smooth muscle cells tend to be in a relaxed state when $K^+$ channels are open. Both glyburide and intracellular ATP can close certain types of $K^+$ channels, causing a depolarization which results in contraction of smooth muscle. Most evidence indicates that glyburide-sensitive $K^+$ channels include ATP-dependent channels, but there is also evidence indicating the existance of other closely related channels (Cook et al., 1990, Potassium Channels, pp. 181-255, Ellis Horwood Pub., Chicester, U.K.).

As shown in the Description section below, for a series of structurally-related relaxing agents tested, there is a good correlation between their apparent affinity for binding to RIN cells and their $ED_{50}$ values for producing a glyburide-reversible relaxation of specific smooth muscle tissue (see FIG. 4). The relaxation produced by these compounds has the characteristics of drugs that open $K^+$ channels because inhibition is prevented by elevated $K^+$ concentrations as expected for a drug acting on a $K^+$ channel. Additionally, glyburide generally reverses or prevents this relaxation in the same concentrations as known in the art for characterized ATP-dependent $K^+$ channels in smooth muscle (Cook et al., 1990, Id.), and these compounds do not effect resting tension.

Furthermore, a structurally unrelated $K^+$ channel agonist, minoxidil sulfate, inhibits binding at appropriate concentrations, while a large number of structurally unrelated drugs that do not act on $K^+$ channels, do not inhibit binding. Specific antagonists of the ATP-dependent $K^+$ channel (glyburide and glypizide) as well as certain non-specific antagonists of $K^+$ channels (quinine, quinidine and TEA) also inhibit binding with a relative potency similar to that reported for their effects on ATP-dependent $K^+$ channels (Longman et al., 1992, Med. Res. Revs., 12:73). The objectives of the present invention include:

1. The use of the present binding assay for the screening of new drugs acting at the specific CMPD-I-sensitive, $K^+$ channel binding site, or at allosterically-linked sites.
2. The use of the disclosed ligand or its analogs, and irreversibly acting analogs, including all optical isomers acting at such binding sites for isolation of the binding proteins related to these sites, and subsequent cloning and expression for their use in drug screening.
3. The use of the disclosed radiolabeled compounds, or their non-radioactive analogs which are detectable by other methods, i.e., fluorescence, spectrophotometry, or other methods for detecting compound-receptor interaction, for the screening of drugs acting at this binding site for any of the proposed uses of drugs acting on $K^+$ channels.

DESCRIPTION OF THE INVENTION

Figure 1:
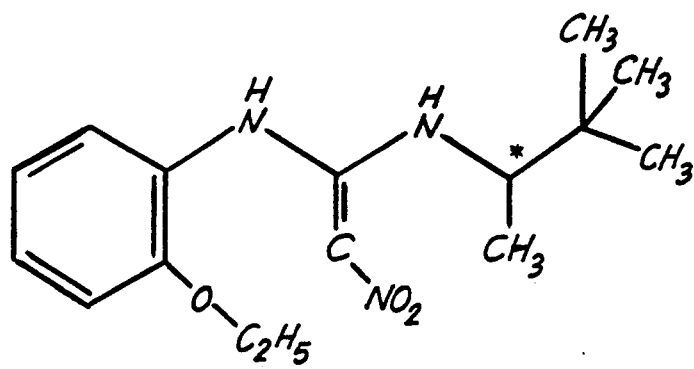
FIG. 1 shows the structure of (+/−) N-(2-ethoxyphenyl)-N'-(1,2,2,-trimethylpropyl)-2-nitroethene-1,1-diamine, the racemate of CMPD-I. The radioligand used in the present assays is the tritiated (+) enantiomer, [$^3$H]CMPD-I.

Ligand binding assays are valuable for the discovery, characterization and development of therapeutic agents. Specific binding of a radiolabeled K$^+$ channel opener, [$^3$H]CMPD-I, to intact RINm5F cells (rat insulinoma, immortalized β-cell line, Chick et al., 1977, Proc. Natl. Acad. Sci. USA, 74:628), was characterized, as shown below. Specific binding was saturable, linear with protein concentration, and reversible. The K$_D$ was 2 nM and B$_{Max}$ 50 fmol/mg total protein as determined by saturation analysis.

The high affinity binding to intact cells was inhibited by pinacidil and a series of diaminonitro-ethylene analogs with an activity sequence correlating well with that for producing glyburide-sensitive relaxation of partially-depolarized rat aorta. Specificity of binding was demonstrated by the inability of several other classes of drugs to inhibit binding.

EXAMPLE 1: Ligand Binding

A) General Description:

The RINm5F cell line (Chick et al., 1977, Id.; and also available from Miles Research Center, Miles Inc., West Haven, Conn.) was maintained in T150 culture flasks and grown in D-MEM (Dulbecco's Modified Eagle Medium), (GIBCO) supplemented with 10% fetal calf serum (GIBCO) and maintained in an atmosphere of 5% CO$_2$/95% air at 37° C. The cells were fed three times a week and passed weekly with 0.25% trypsin/0.02% EDTA (JRH Biosciences, Lenexa, Kans.).

For intact cell binding experiments, RINm5F cells were plated onto 60 mm polystyrene petri dishes (Corning) at 5×10$^6$ cells/dish and grown for 3 days without a change of media. Alternatively, cells were seeded 1×10$^6$ cells/dish and grown for 7 days with the last feeding two days prior to use. Final cell density was 10-20 ×10$^6$ cells/dish.

[$^3$H]CMPD-I was synthesized by dehalogenating the following compound (I) with tritium gas using a Pd catalyst:

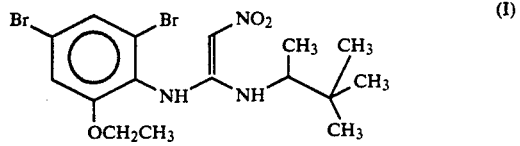

(I)

The tritium labeled racemate was separated into enantiomers by a chiral HPLC column.

For binding experiments cells were incubated in a partially depolarizing Hanks-bicarbonate buffer solution (pH 7.4 at 37° C.) of the following composition in mM: NaCl, 105; KCl, 20; MgCl$_2$, 0.98; CaCl$_2$, 1.26; HEPES, 20; glucose, 5.56; KH$_2$PO$_4$, Na$_2$HPO$_4$, 0.63; NaHCO$_3$, 4.16 (aerated with 5%CO$_2$/95%O$_2$).

Intact cell binding was performed with the cells attached to the dishes. Binding was terminated by three successive 3 ml washes of cold (4° C.) buffer. Cells were removed from the dish in 1.6 ml of 0.5 N NaOH, briefly sonicated and radioactivity was quantitated with a liquid scintillation counter using 10 ml cocktail (Ultima Gold, Packard).

Statistical analysis to determine K$_D$ and B$_{Max}$ was accomplished using nonlinear regression (Enzfitter, Elsevier-Biosoft, Cambridge, UK). IC$_{50}$ values were determined using a sigmoidal fit of mean percent inhibition versus log of concentration.

B) Procedure:

Petri dishes were removed from the incubator, media was aspirated and the cells were washed (x2) with 3 ml oxygenated (5%CO$_2$/95%O$_2$) Hanks Buffer (37° C.). Cells were allowed to equilibrate in buffer at least 10 minutes. The buffer was removed and replaced with [$^3$H]CMPD-I in 3 ml Hanks buffer and test drug or vehicle at the desired concentration. Dishes were incubated at 37° C., in an atmosphere of 5% CO$_2$/95% for 90 minutes. Bound radioligand was separated from free by aspirating the buffer and washing the cells rapidly (x3) with 3 ml ice cold (4° C.) Hanks Buffer.

Cells were then removed and solubilized with the addition of 1.6 ml 0.5N NaOH. Dishes were mounted on an orbit shaker (Lab Line) and rotated at 100–125 rpm for 20–45 minutes until the cells would detach from the plates. The contents of each dish was transferred to a 12×75 mm glass culture tube and sonicated for 5–10 seconds using a micro ultrasonic cell disrupter (Kontes, 3.2×48 mm probe, output setting 40–50). The solutions were vortexed and an aliquot (10 μ') from each tube was removed for total protein determination. The remainder (1.59 ml) was transferred to a 20 ml vial with 10 ml Ultima Gold (Packard) scintillation cocktail and mixed until the aqueous phase cleared. Each sample was counted for at least one minute by a liquid scintillation system set for counting tritium. Total protein content of each dish was determined by the method of Bradford with bovine serum albumin used as the standard.

Specific binding was determined by calculating specific cpm: Total cpm (vehicle) - Nonspecific cpm (1–10 μM CMPD I). Percent Inhibition of specific binding by test compounds was determined by calculating:

100−[(Cpm (with Drug)−Nonspecific cpm÷Specific cpm)×100](Basic program)

Free and Bound radioligand was calculated (Basic program) and a saturation curve based on a nonlinear regression fit of the data was used to determine a K$_D$ (nM) and B$_{max}$ (fmoles/mg total cellular protein) of binding (Enzfitter, Id.).

Mean percent inhibition of binding at the concentrations tested for each drug was fit to a sigmoidal function. IC$_{50}$ values were calculated from the plot of the fraction of maximal inhibition versus Log of concentration (Enzfitter, Id.).

EXAMPLE 2: Aortic Relaxation

A) General Description:

Male Long-Evans Hooded rats (200–400 g) were sacrificed by acute decapitation. Thoracic aortae were rapidly removed and placed in an oxygenated (100% $O_2$) physiological saline solution (PSS) (pH 7.4) of the following composition in mM: NaCl, 130; KCl, 5.9; $MgCl_2$, 1.2; $CaCl_2$, 0.8; HEPES, 22 and glucose, 11.1. The aortae were trimmed of fat, cut into rings 3 mm in length, mounted in an organ bath containing 10 ml of oxygenated PSS at 37° C. and stretched to a resting tension of 2.0 g.

The aortae were depolarized with 20 mM KCl and after contractile response had stabilized, vasodilators were added. The vasorelaxation produced by the drugs was reversed by glyburide (a potent antagonist of ATP-dependent K+ channels, as described above).

B) Procedure:

Prior to the aortic preparation, the instrument to measure changes in aortic tension was set up and each channel was statically calibrated for linearity using Class S metric weights from 1 to 5 grams, the range consistent with changes observed in this study. This instrument translates isometric changes in tension over time to an electrical signal expressed as a tracing that can be quantified by peak height.

An adult male Long-Evans rat was sacrificed by decapitation and a longitudinal incision was made from the lower abdomen forward separating the rib cage at the sternum. The ribs were folded back and the descending branch of the aorta was removed from the aortic arch to the common iliac arteries. This section (20–25 mm) was transferred to a glass petri dish containing oxygenated PSS buffer at room temperature. Under low magnification, the adherent fatty tissue and blood clots were carefully removed from the vessel and the aorta was cut into ring segments of 3 mm. The interior of the each segment was rubbed lightly with a wooden applicator to remove the endothelium.

The aortic rings were transferred to another petri dish with fresh PSS and were mounted on 20 gauge hooks looped through the segment and attached to a 1/16" thick stainless steel rod. A length of 4–0 silk with a tied loop at both ends was used to connect the ring to the force transducer in the organ bath. Once installed in the organ bath, a tensioner knob was used to raise the force transducer until the ring was stretched to a resting tension of 2 grams.

The tissue was maintained in a volume of 10 ml PSS at 37° C. and constantly oxygenated in light bubbling with 100% $O_2$. After a 90 minute equilibration the resting tension was readjusted to the baseline level. The rings were challenged with an addition of KCl (100 μl of a 2M stock) which was added with a micropipet to the surface of the buffer, which raised the K+ concentration 20 mM. This addition caused a depolarization-induced increase in tension over basal that stabilized after 10–15 minutes between 1–2 grams on average. The increase in tension was stable for hours. Washing the tissue by draining the buffer from the organ bath and replacing it with fresh buffer resulted in a return of tension to baseline levels (a second depolarization-produced maximal contractile response).

Following another wash, a third K+ contraction was initiated to be tested for response with drug additions. Specificity of relaxation was tested for reversal by 1–10 μM glyburide. Percent relaxation of putative K+ channel agonists was calculated as follows:

100−[(Peak Height (mm) after Drug÷Initial Peak Height (mm) after 20 mM K+)×100]

Percent of initial contraction following drug addition was plotted on a probit scale versus Log of concentration and the $ED_{50}$ was extrapolated.

Figure 2:
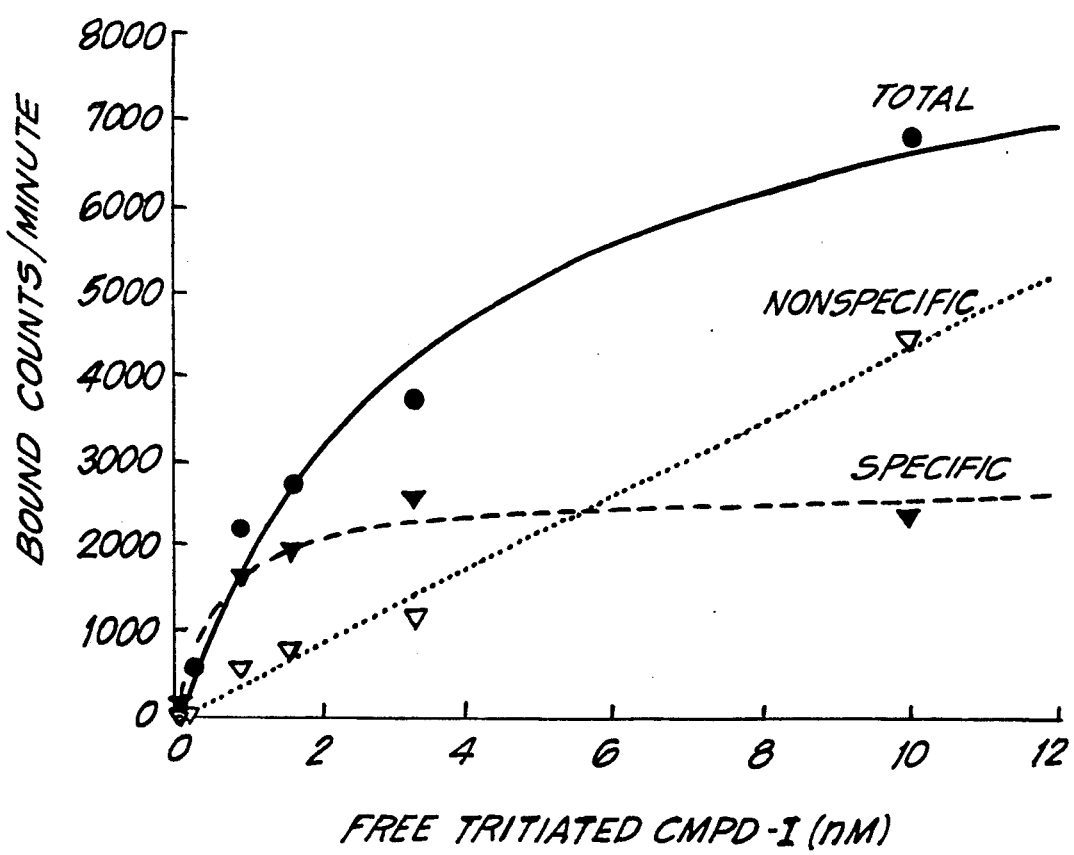
FIG. 2 graphically depicts the binding of [$^3$H]CMPD-I to intact RINm5F cells as a function of increasing concentration. Data is representative of three experiments. Each point was assayed in duplicate and nonspecific binding was determined in the presence of 3 μM CMPD-I.
Figure 3:
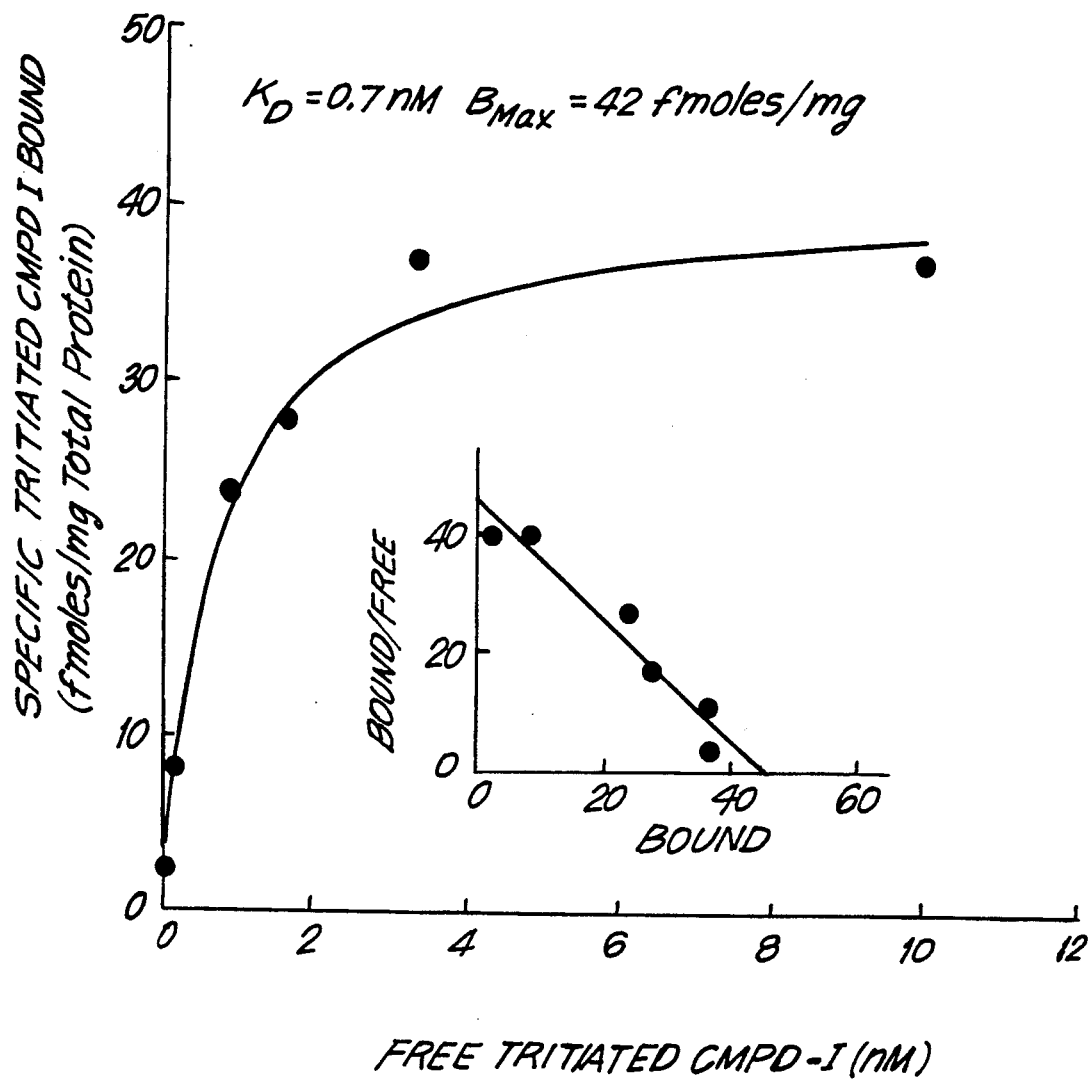
FIG. 3 shows specific binding of [$^3$H]CMPD-I to intact RINm5F cells as a function of increasing concentration. Nonspecific binding was determined in the presence of 3 μM CMPD-I. The inset shows Scatchard transformation of the same data.

Binding of [$^3$H]CMPD-I to intact RINm5F cells was specific and saturable (see FIG. 2). Scatchard analysis indicated a single binding site with an apparent $K_D$ of 0.7 nM and a $B_{Max}$ of 42 fmol/mg total protein (see FIG. 3). Two additional experiments gave $K_D$ values of 2.3 and 2.4 nM and $B_{Max}$ values of 33 and 68 fmol/mg, respectively.

Figure 4A:
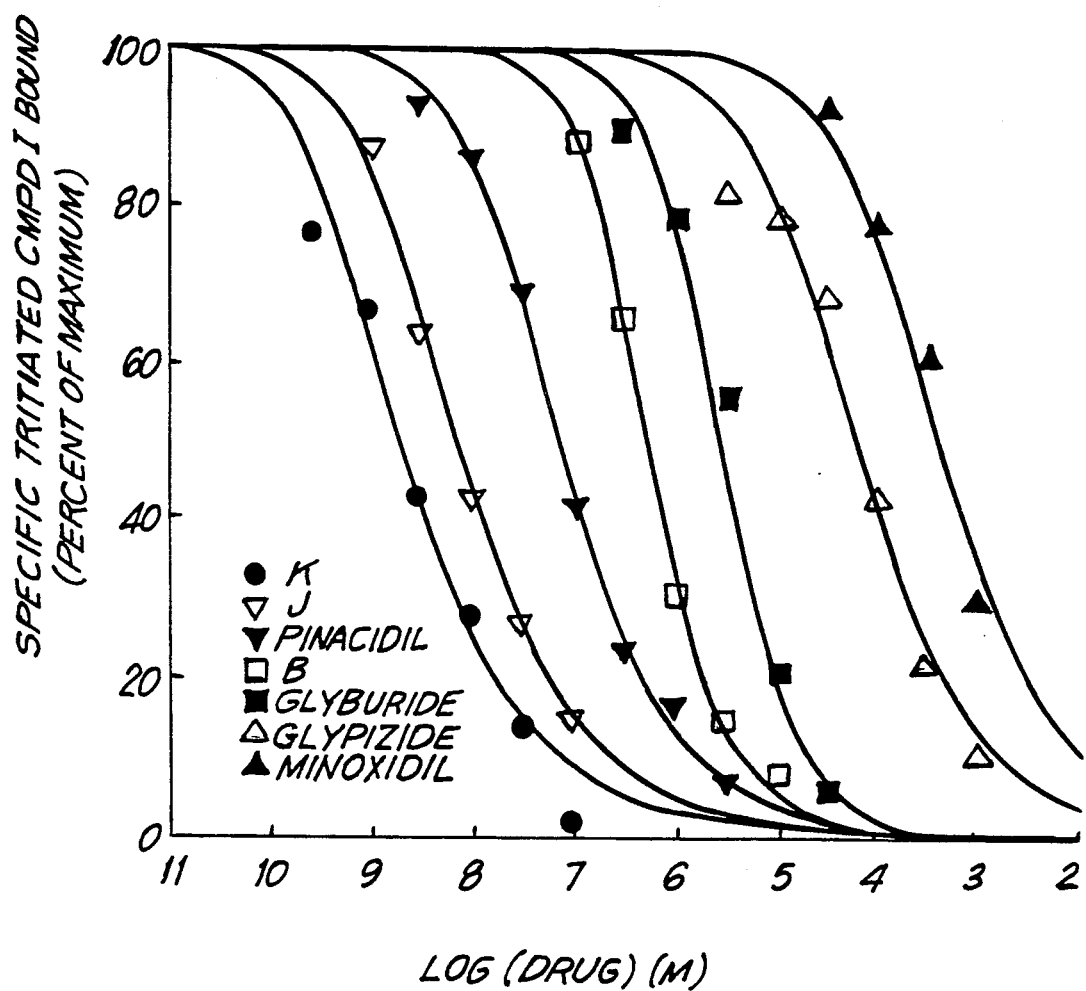
FIG. 4A graphically depicts inhibition of specific [$^3$H]CMPD-I (2 nM) binding to RINm5F cells by a series of K$^+$ channel agonists and antagonists.
Figure 4B:
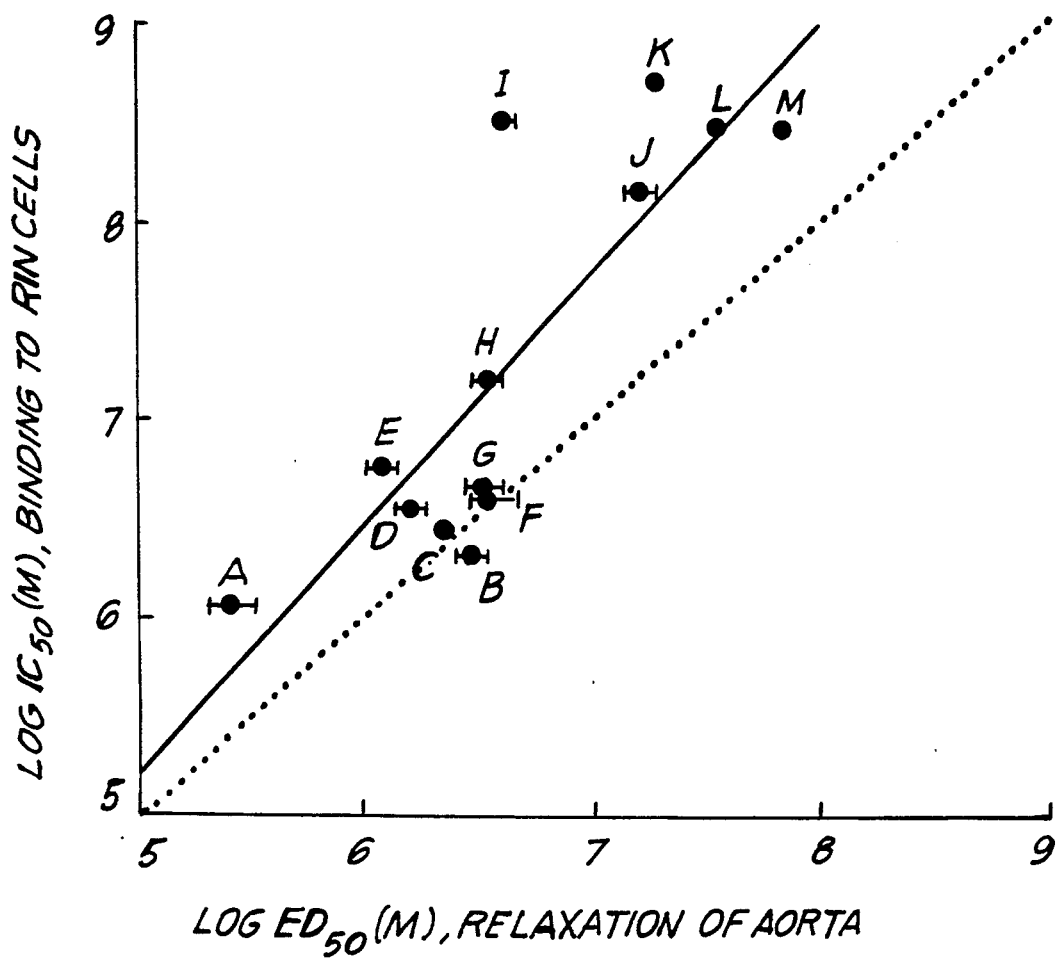
FIG. 4B shows correlation for a series of K$^+$ channel agonists, between inhibition (IC$_{50}$) of [$^3$H]CMPD-I binding to RINm5SF cells and relaxation (ED$_{50}$) of test smooth muscle which was precontracted with 20 mM KCl; r=0.83.

FIG. 4A graphically depicts inhibition of specific [$^3$H]CMPD-I (2 nM) binding to RINm5F cells by a series of K+ channel agonists and antagonists tested. Each point from 10–85% inhibition is the mean of 2–4 determinations performed in duplicate. Compounds K, J and B are analogs of N-(2-ethoxyphenyl)-N'-(1,2,2,-trimethylpropyl)-2-nitroethene-1,1-diamine (see FIG. 1), with the following phenyl substitutions: for compound K, 3,5-methoxy; for compound J, 2-ethoxy, 4,6-bromo; and compound B is unsubstituted. FIG. 4B shows correlation for a series of K+ channel agonists, between inhibition ($IC_{50}$) of [$^3$H]CMPD-I binding to RINm5F cells and relaxation ($ED_{50}$) of test smooth muscle which was precontracted with 20 mM KCl; r=0.83. $IC_{50}$ values are calculated from a sigmoidal fit of the mean percent inhibition of 2–4 data points performed in duplicate for each concentration tested. $ED_{50}$ values were graphically extrapolated and the mean values ± standard error are shown.

Compound H is pinacidil. Compound L is the racemate, (+/−) N-(2-ethoxyphenyl)-N'-(1,2,2,-trimethylpropyl)-2-nitroethene-1,1-diamine; compound M, the (+) enantiomer, CMPD-I; and compound I, the (−) enantiomer.

Compounds A–G, J, and K are analogs of N-(2-ethoxyphenyl)-N'-(1,2,2,-trimethylpropyl)-2-nitroethene-1,1-diamine (see FIG. 1), with the following phenyl substitutions: for compound A, unsubstituted phenyl and further lacking a methyl group on the asymmetric carbon (\*); compound B has an unsubstituted phenyl ring; compound C, 4-hydroxy; compound D, 3-methoxy; compound E, 4-ethyl; compound F, 4-methoxy; compound G, 2,6-methyl; compound J, 2-ethoxy, 4,6-bromo; and compound K, 3,5-methoxy.

What we claim is:

1. A method for identifying compounds capable of specific binding to K+ channels sensitive to tritiated (+)-N-(2-ethoxyphenyl)-N'-(1,2,2-trimethyl propyl)-2-nitroethene-1,1-diamine ([$^3$H]CMPD-I), said method comprising the following steps:

(a) preparing a culture of a selected rat insulinoma (RIN) cell line;
   (b) adding [$^3$H]CMPD-I;
   (c) introducing a test compound; and
   (d) determining inhibition of specific binding of [$^3$H]CMPD-I by said test compound, wherein inhibition indicates the capacity of said test compound to specifically bind to said K+ channels sensitive to [$^3$H]CMPD-I.

2. The method of claim 1, wherein said selected RIN cell line is RINm5F.

3. A method for screening compounds capable of regulating K+ channels sensitive to tritiated (+)-N-(2-ethoxyphenyl)-N'-(1,2,2-trimethylpropyl)-2-nitroethene-1,1-diamine ([$^3$H]CMPD-I), said method comprising the following steps:

(a) preparing a selected rat insulinoma (RIN) cell line culture in an appropriate buffer and cell density;

(b) replacing said buffer with a solution containing [$^3$H]CMPD-I;

(c) adding a test compound at a selected concentration to form a mixture;

(d) incubating said mixture at selected conditions;

(e) separating bound [$^3$H]CMPD-I from free [$^3$H]CMPD-I in a suitable manner such as to form a counting sample;

(f) counting said sample with a suitable detector for tritium; and (g) determining inhibition of specific binding of [$^3$H]CMPD-I by said test compound, wherein inhibition indicates the capacity of said test compound to regulate k+ channels sensitive to [$^3$H]CMPD-I.

4. The method of claim 3, wherein said selected cell line culture are cells in suspension or attached cells.

5. The method of claim 3, wherein said selected cell line is RINm5F.

* * * * *

UNITED STATES PATENT AND TRADEMARK OFFICE
CERTIFICATE OF CORRECTION

PATENT NO. : 5,328,830

DATED : July 12, 1994

INVENTOR(S) : Janis, et al.

It is certified that error appears in the above-identified patent and that said Letters Patent is hereby corrected as shown below:

Col. 3, line 42   After " Id.; " insert -- a sample of which was deposited with the American Type Culture Collection, Rockville, Maryland, on April 6, 1994, under accession number CRL 11605; --

Signed and Sealed this

Eleventh Day of October, 1994

Attest:

BRUCE LEHMAN

*Attesting Officer*     *Commissioner of Patents and Trademarks*